United States Patent
Yoshida

(10) Patent No.: US 10,231,672 B2
(45) Date of Patent: Mar. 19, 2019

(54) ECG SIGNAL PROCESSING APPARATUS, MRI APPARATUS, AND ECG SIGNAL PROCESSING METHOD

(71) Applicant: TOSHIBA MEDICAL SYSTEMS CORPORATION, Otawara-Shi (JP)

(72) Inventor: Takami Yoshida, Kawasaki (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 397 days.

(21) Appl. No.: 15/228,318

(22) Filed: Aug. 4, 2016

(65) Prior Publication Data

US 2017/0035363 A1    Feb. 9, 2017

(30) Foreign Application Priority Data

Aug. 6, 2015   (JP) .................. 2015-156409

(51) Int. Cl.
*A61B 5/00* (2006.01)
*A61B 5/0456* (2006.01)
(Continued)

(52) U.S. Cl.
CPC .......... *A61B 5/7203* (2013.01); *A61B 5/0402* (2013.01); *A61B 5/0456* (2013.01); *A61B 5/055* (2013.01); *A61B 2560/0475* (2013.01)

(58) Field of Classification Search
None
See application file for complete search history.

(56) References Cited

U.S. PATENT DOCUMENTS 4,694,837 A    9/1987   Blakeley et al.
5,436,564 A *  7/1995   Kreger ............... A61B 5/0424
                                                         128/901
(Continued)

FOREIGN PATENT DOCUMENTS

JP    3-173534      7/1991
JP    2004-329669   11/2004

OTHER PUBLICATIONS

R. Abacherli, et al. "Suppression of MR gradient artefacts on electrophysiological signals based on an adaptive real-time filter with LMS coefficient updates", MAGMA, 18:41-50, 2005., 10 pages.

*Primary Examiner* — Brian T Gedeon
(74) *Attorney, Agent, or Firm* — Oblon, McClelland, Maier & Neustadt, L.L.P.

(57) ABSTRACT

In one embodiment, an ECG signal processing apparatus is configured to be connected with an electrocardiograph and an MRI apparatus and includes memory circuitry and processing circuitry configured to (a) store a parameter of an ECG signal as a first parameter in the memory circuitry, the ECG signal being acquired from the electrocardiograph operating in combination with the MRI apparatus in a period during which a gradient pulse is not applied by the MRI apparatus, (b) implement an adaptive filter for estimating noise mixed into the ECG signal due to the gradient pulse, by using the first parameter stored in the memory circuitry and a gradient magnetic field signal acquired from the MRI apparatus in a period during which the gradient pulse is applied, and (c) remove the noise mixed into the ECG signal in the period during which the gradient pulse is applied, by using estimated noise.

12 Claims, 15 Drawing Sheets

(51) Int. Cl.
*A61B 5/0402* (2006.01)
*A61B 5/055* (2006.01)

(56) References Cited

U.S. PATENT DOCUMENTS

| | | | |
|---|---|---|---|
| 8,626,266 B1 * | 1/2014 | Frank | A61B 5/055 600/413 |
| 2008/0004537 A1 * | 1/2008 | Uutela | A61B 5/0428 600/509 |
| 2014/0171783 A1 * | 6/2014 | Schmidt | G01R 33/5673 600/413 |

* cited by examiner

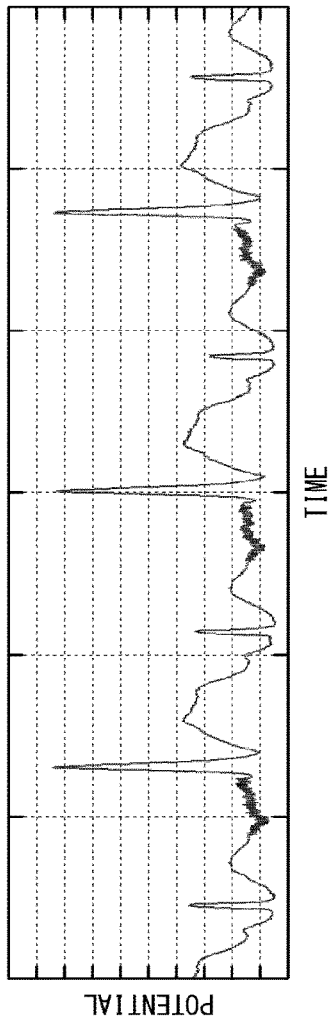
FIG. 9A  ECG SIGNAL (INPUT)
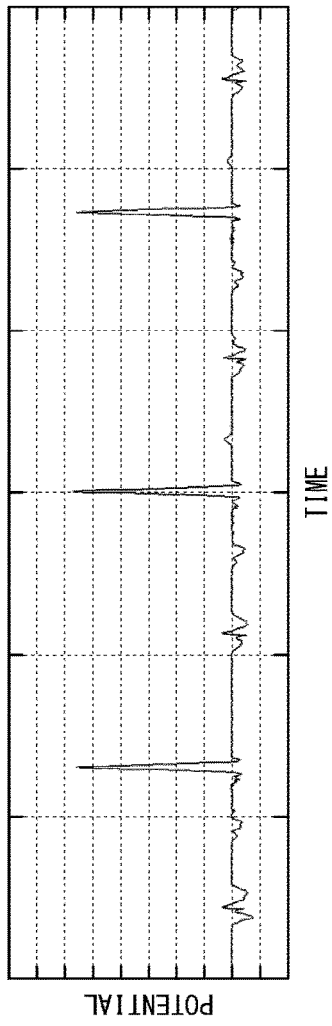
FIG. 9B  ECG SIGNAL SUBJECTED TO NOISE REMOVAL PROCESSING WITHOUT USING REFERENCE PARAMETER
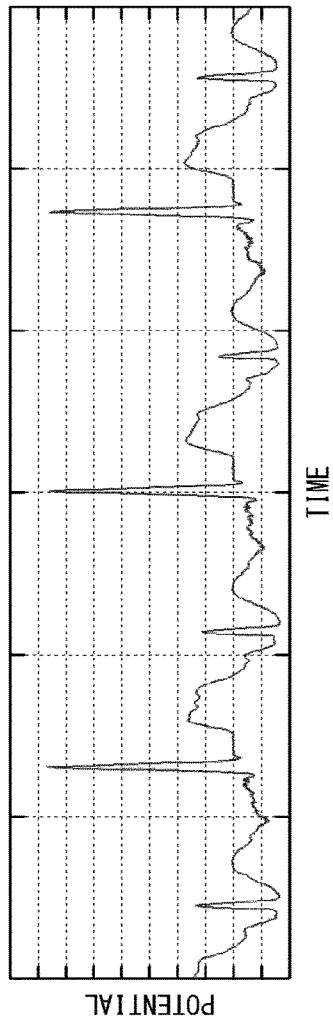
FIG. 9C  ECG SIGNAL SUBJECTED TO NOISE REMOVAL PROCESSING BY USING REFERENCE PARAMETER

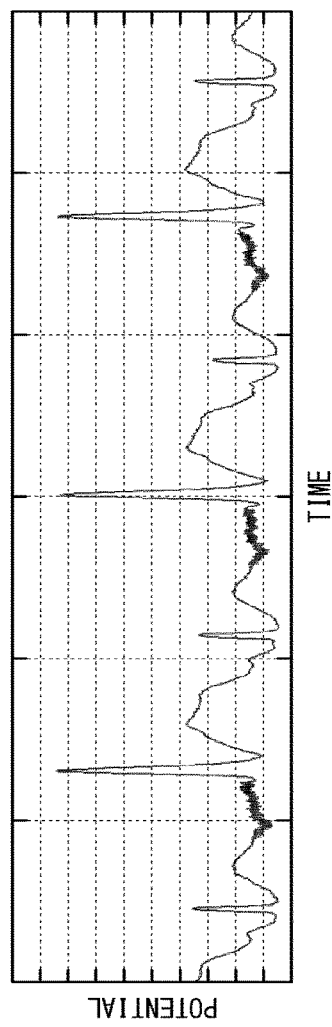
FIG. 12A  ECG SIGNAL (INPUT)
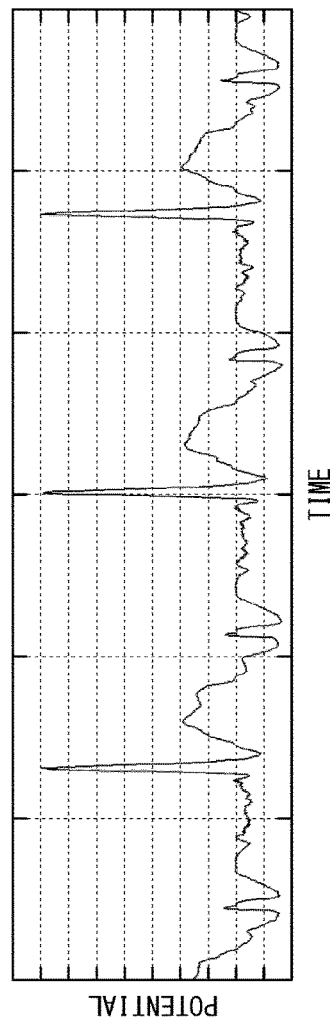
FIG. 12B  ECG SIGNAL SUBJECTED TO NOISE REMOVAL PROCESSING (EFFECT OF NOISE REMOVAL PROCESSING IN FREQUENCY DOMAIN)

ECG SIGNAL PROCESSING APPARATUS, MRI APPARATUS, AND ECG SIGNAL PROCESSING METHOD

CROSS-REFERENCE TO RELATED APPLICATION

This application is based upon and claims the benefit of priority from Japanese Patent Application No. 2015-156409, filed on Aug. 6, 2015, the entire contents of which are incorporated herein by reference.

FIELD

Embodiments described herein relate generally to an ECG (electrocardiogram) signal processing apparatus, an MRI (Magnetic Resonance Imaging) apparatus, and an ECG signal processing method.

BACKGROUND

An electrocardiograph is a device whose electrodes are set on a biological body to measure an electric potential difference between the electrodes. A signal measured by an electrocardiograph is referred to as an ECG (Electrocardiogram) signal and is widely used in the medical field. An ECG signal has waveforms referred to as a P-wave, an R-wave, a QRS complex wave, and a T-wave, for example. Since these waveforms are used for a synchronization signal of a medical imaging apparatus capable of ECG synchronization imaging in addition to diagnosis of various types of cardiac disease, automatic detection of such waveforms is important in terms of industrial applications.

For example, in cardiac image diagnosis with the use of an MRI apparatus, imaging is performed at each timing synchronized with systole or diastole by using a synchronization signal (which is also referred to as a trigger signal) detected from an ECG signal. Such imaging is called ECG synchronization imaging.

In an ECG signal acquired from an examinee set inside an MRI apparatus, noise is mixed due to effects of magnetic fields generated by the MRI apparatus and this degrades signal-to-noise ratio. In particular, strong noise is mixed during imaging, and even an R-wave which is the most distinct waveform in an ECG signal becomes difficult to be stably detected in some cases. In order to robustly detect an R-wave with respect to noise, it is effective to enhance cardiac action potential in an acquired ECG signal and suppress noise while keeping the cardiac action potential undisturbed.

Noise which degrades performance of detecting an R-wave is generated due to RF (Radio Frequency) pulses and switching of gradient magnetic fields in association with imaging. Magnetic flux density around an electrocardiograph and its electrodes temporally changes, which generates induced electromotive force, and the induced electromotive force is mixed into an ECG signal as noise. Thus, there is similarity between characteristics of noise and characteristics of gradient magnetic fields and/or RF pulses. Accordingly, what type of noise is mixed into an ECG signal can be estimated to some extent from a gradient-magnetic-field control signal. So far, a method of estimating noise mixed into an ECG signal from a gradient-magnetic-field control signal by using an adaptive filter and removing the noise has been proposed.

However, in a conventional adaptive filter, amount of eliminated noise is not sufficient in some cases. Additionally, in a conventional adaptive filter, noise is excessively removed and cardiac action potential is negatively affected to a great extent in some cases.

BRIEF DESCRIPTION OF THE DRAWINGS

In the accompanying drawings:

FIG. 9A to FIG. 9C are graphs illustrating temporal change of potential by which effects of the ECG signal processing apparatus according to the first embodiment are indicated;

FIG. 12A and FIG. 12B are graphs illustrating temporal change of potential, by which effects of the ECG signal processing apparatus of the second embodiment configured to perform noise removal on each ECG signal in a frequency domain are indicated;

DETAILED DESCRIPTION

In one embodiment, an ECG signal processing apparatus is configured to be connected with an electrocardiograph and an MRI apparatus and includes memory circuitry and processing circuitry configured to (a) store a parameter of an ECG signal as a first parameter in the memory circuitry, the ECG signal being acquired from the electrocardiograph operating in combination with the MRI apparatus in a period during which a gradient pulse is not applied by the MRI apparatus, (b) implement an adaptive filter for estimating noise mixed into the ECG signal due to the gradient pulse, by using the first parameter stored in the memory circuitry and a gradient magnetic field signal acquired from the MRI apparatus in a period during which the gradient pulse is applied, and (c) remove the noise mixed into the ECG signal in the period during which the gradient pulse is applied, by using noise estimated by the adaptive filter.

Hereinafter, embodiments of an ECG signal processing apparatus, an MRI apparatus, and an ECG signal processing method will be described with reference to the accompanying drawings. In the following embodiments, it is assumed that components of the same reference number operate in a manner similar to each other, and duplicate description is omitted.

First Embodiment

Figure 1:
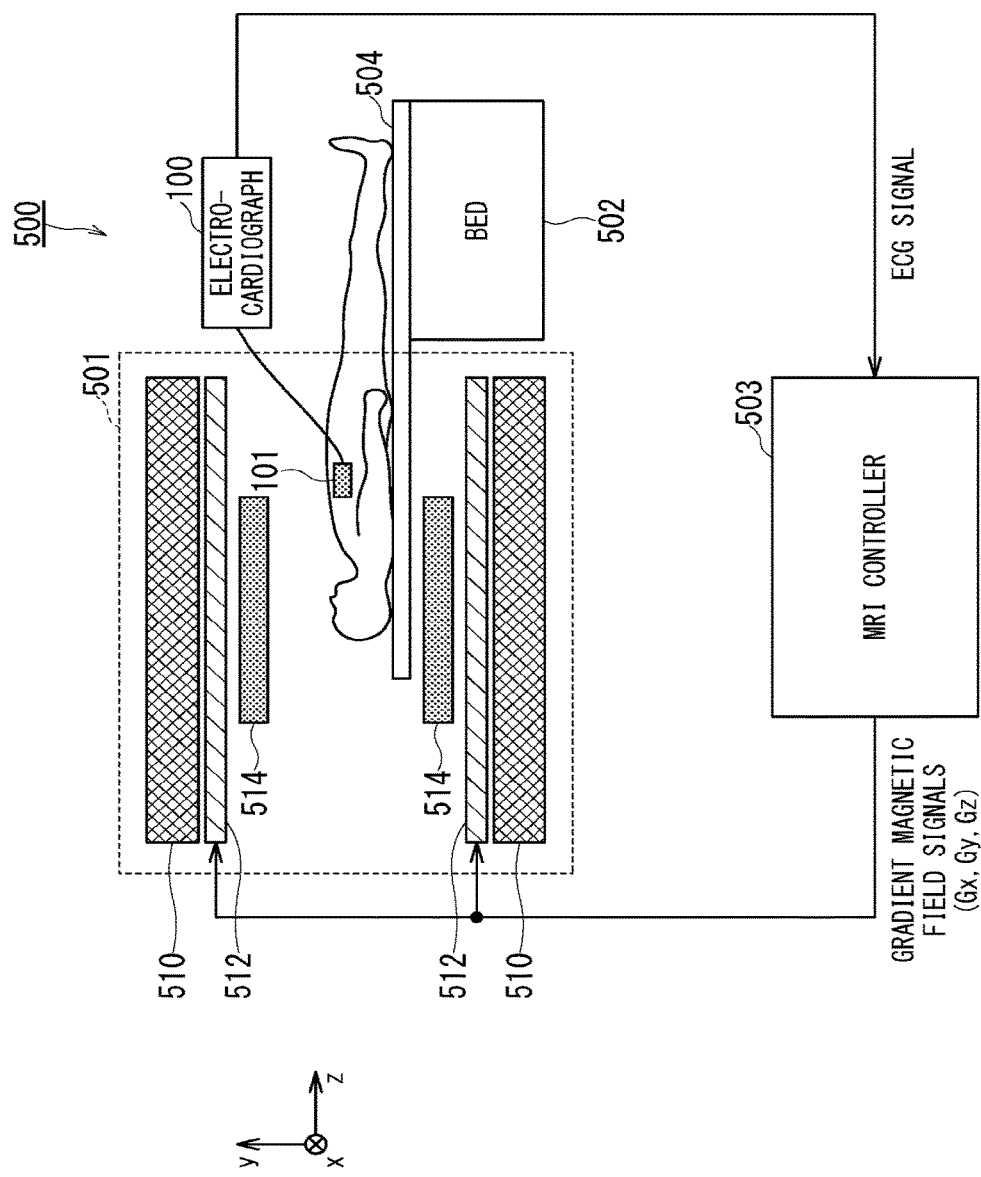
FIG. 1 is a schematic diagram illustrating concept of conventionally performed ECG synchronization imaging using an MRI apparatus.

FIG. 1 is a schematic diagram illustrating concept of conventionally performed ECG synchronization imaging using an MRI apparatus. An MRI apparatus 500 includes, for example, a gantry 501, a bed 502, and an MRI controller 503. The gantry 501 includes cylindrical components such as a static magnetic field magnet 510, a gradient coil 512, and an RF coil 514.

An object, e.g., a patient lying on the table 504 of the bed 502 is imaged after being moved into the internal space of the cylindrical structure of the gantry 501 (referred to as a bore). During imaging, an RF magnetic field from the RF coil 514 is applied to the object and gradient magnetic fields (i.e., gradient pulses) in the triaxial directions perpendicular to each other are applied to the object. In order to apply the gradient pulses, gradient magnetic field signals Gx, Gy, and Gz corresponding to the three gradient magnetic fields in the respective triaxial directions perpendicular to each other are supplied from the MRI controller 503 to the gradient coil 512.

In the case of ECG synchronization imaging, a synchronization signal is generated based on an ECG signal outputted from an electrocardiograph 100 and each RF magnetic field and each gradient pulse are applied to the object at each timing synchronized with this synchronization signal. The electrodes 101 of the electrocardiograph are attached to body surface of the object inside the bore, in general.

As described above, since each RF magnetic field and each gradient pulse are also applied to the electrodes 101 during imaging, noise is superimposed on each ECG signal outputted from the electrocardiograph 100. In particular, considerably large noise is superimposed on each ECG signal in association with application of the gradient pulses.

Figure 2:
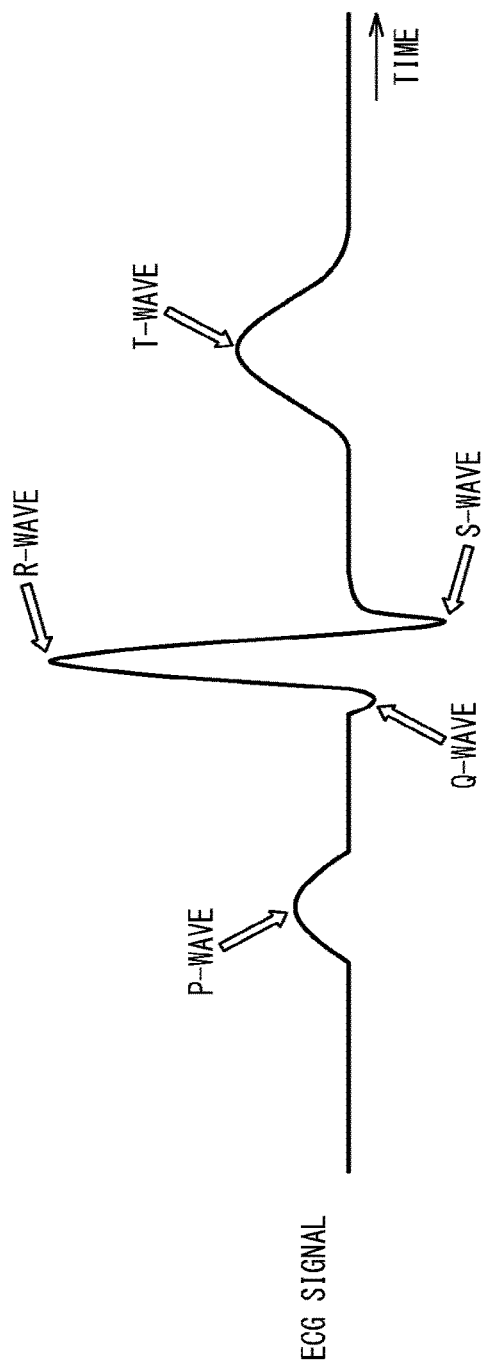
FIG. 2 is a schematic diagram illustrating a waveform of an ECG signal when noise is not superimposed thereon.

FIG. 2 is a schematic diagram illustrating a waveform of an ECG signal when noise is not superimposed thereon. As shown in FIG. 2, an ECG signal has specific waveforms such as a P-wave, a Q-wave, an R-wave, an S-wave, and a T-wave, and these waveforms correspond to cardiac active potential. In each of the embodiments below, description will be given of a case where each R-wave out of these specific waveforms is detected. Note that detecting an R-wave is only one aspect of possible embodiments and the ECG signal processing apparatus of each embodiment can detect other waveforms such as a P-wave and a T-wave aside from an R-wave.

Figure 3:
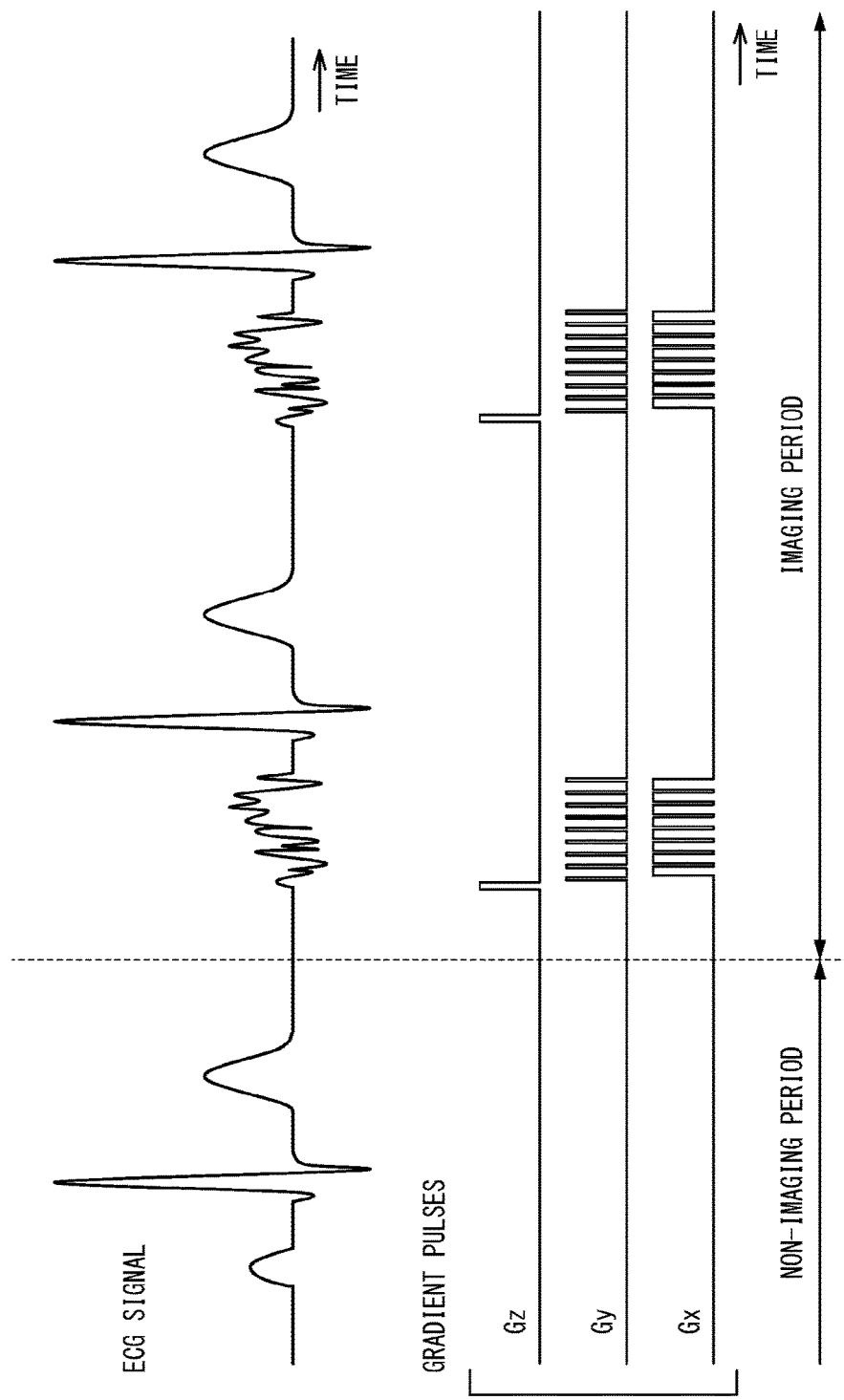
FIG. 3 is a schematic diagram illustrating an ECG waveform, when gradient pulses are applied and noise is superimposed on the ECG waveform due to the gradient pulses.

FIG. 3 is a schematic diagram illustrating an ECG waveform when gradient pulses are applied. During imaging, RF pulses as well as gradient pulses Gx, Gy, and Gz illustrated in the bottom part of FIG. 3 are applied. Hereinafter, a period during which RF pulses and gradient pulses are applied is referred to as "an imaging period", and a period during which neither an RF pulse nor a gradient pulse is applied is referred to as "a non-imaging period".

In an MRI apparatus, imaging data, i.e., magnetic resonance signals are acquired by executing a pulse sequence in which intensity and application timings of respective gradient pulses and respective RF pulses are determined. Additionally, an imaging sequence from the start of a pulse sequence to the completion of acquisition of predetermined imaging data by repeating necessary number of TR (Repetition Time) is referred to as a protocol, for example.

In the present specification, "an imaging period" means, for example, a period in which a pulse sequence is executed and "a non-imaging period" means, for example, a period in which a pulse sequence is not executed. For example, a period prior to start of the first protocol included in a series of examinations and an interval between one protocol and the subsequent protocol are non-imaging periods. Additionally, a period after attaching surface coils to an object and before start of a prescan for tuning is also a non-imaging period. Further, there can be cases where a non-imaging period is included in an execution period of a pulse sequence corresponding to one protocol. For example, application of RF pulses and gradient pulses is interrupted for plural heartbeats in order to wait recovery of longitudinal magnetization in some cases, and such an interruption period is also a non-imaging period.

In an imaging period, as illustrated in the upper part of FIG. 3, noise is superimposed on an ECG signal. By contrast, in a non-imaging period, since gradient pulses Gx, Gy, Gz and RF pulses are not applied, noise is not superimposed on an ECG signal and the ECG signal becomes a waveform consisting of only the cardiac action potential such as an R-wave.

Although an R-wave is more distinct than other waveforms in the ECG signal illustrated in FIG. 3, a peak value of an R-wave is so small as to be indistinguishable from a P-wave and/or a T-wave in some patients with cardiac disease. Thus, when noise is superimposed on an ECG signal of such patients, it becomes more difficult to detect an R-wave as a synchronization signal from each ECG signal of such patients.

An ECG signal processing apparatus of each embodiment suppresses such noise that is superimposed on an ECG signal.

Figure 4:
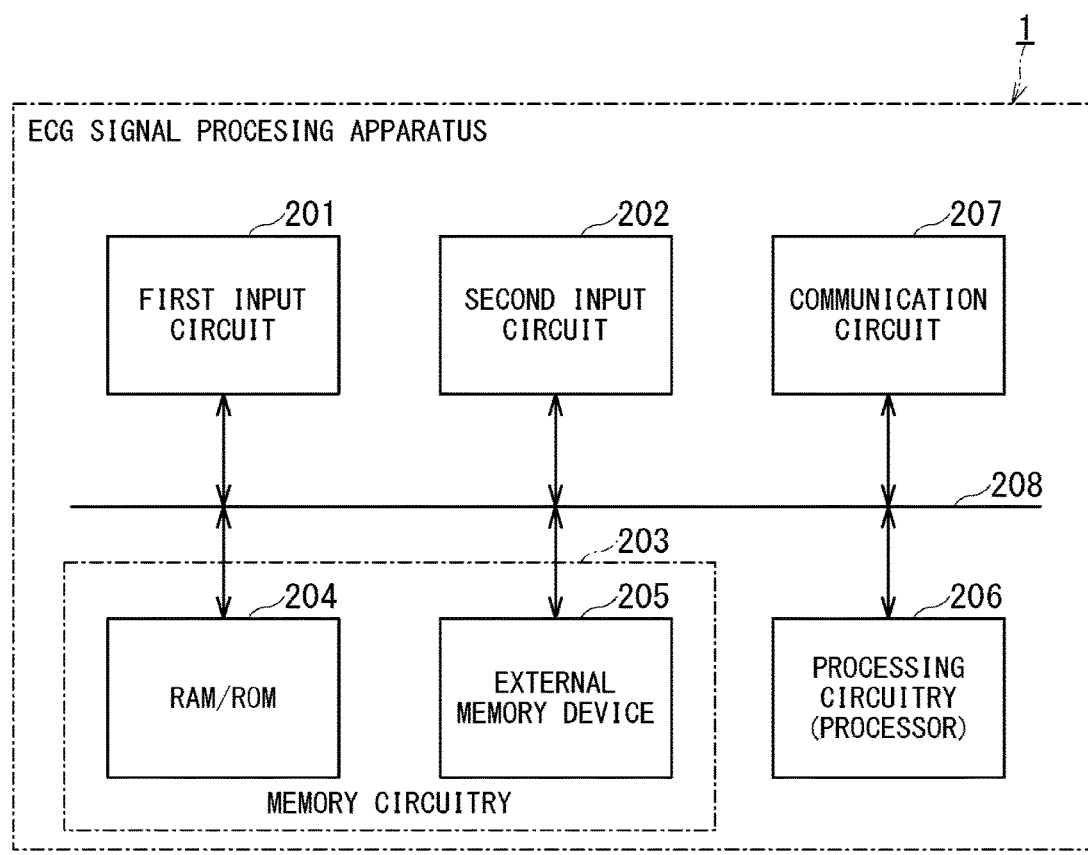
FIG. 4 is a schematic block diagram illustrating hardware configuration of an ECG signal processing apparatus according to the first embodiment.

FIG. 4 is a schematic block diagram illustrating hardware configuration of an ECG signal processing apparatus 1 of the first embodiment. The ECG signal processing apparatus 1 includes a first input circuit 201, a second input circuit 202, memory circuitry 203, processing circuitry 206, and a communication circuit 207.

Figure 5:
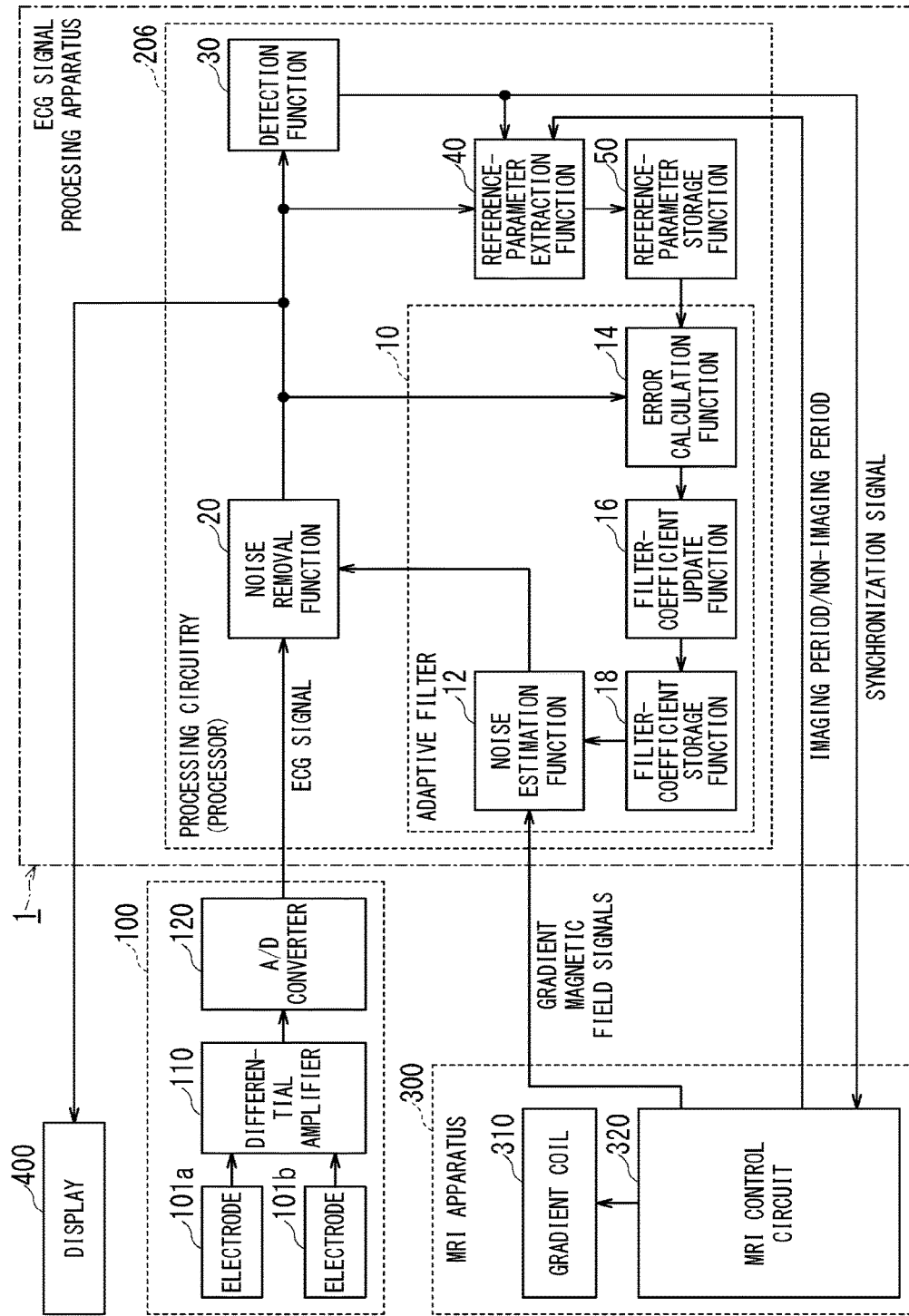
FIG. 5 is the first functional block diagram of the ECG signal processing apparatus according to the first embodiment.

The first input circuit 201 acquires ECG signals from an electrocardiograph 100 (see FIG. 5). The second input circuit 202 acquires gradient magnetic field signals from an MRI apparatus 300. The gradient magnetic field signals are control signals for generating the respective gradient magnetic fields Gx, Gy, and Gz. Thus, each of the gradient magnetic field signals has a waveform similar to the pulse waveform of each of the gradient magnetic fields Gx, Gy, and Gz. The gradient magnetic field signals are composed of three signals corresponding to the respective gradient magnetic fields Gx, Gy, and Gz. Hereinafter, the three gradient magnetic field signals are arbitrarily referred to as gx, gy, and gz.

The memory circuitry 203 includes an external memory device 205 and a ROM/RAM 204 which includes a ROM (Read Only Memory) and/or a RAM (Random Access Memory). The external memory device 205 is a memory medium such as a HDD (Hard Disk Drive), an optical disc, and a magnetic disc. The ROM/RAM 204 and the external memory device 205 store various types of data and various types of programs.

The processing circuitry 206 is a processor such as a CPU (Central Processing Unit). The processing circuitry 206 implements various type of functions as described below by executing programs stored in the memory circuitry 203.

The processing circuitry 206 may be configured of hardware such as an ASIC (Application Specific Integration Circuit) and an FPGA (Field-Programmable Gate Array), and the processing circuitry 206 can also implement various types of functions even in the case of being configured as the above-described hardware. Additionally, the processing circuitry 206 can implement various types of functions by combining hardware processing of, e.g., an ASIC and an FPGA and software processing of a processor.

The communication circuit 207 performs communication with external devices. Additionally, a bus 208 interconnects each of the above-described circuits.

FIG. 5 is the first functional block diagram of the ECG signal processing apparatus 1. In FIG. 5, the electrocardiograph 100, the MRI apparatus 300, and the display 400 are also illustrated. The electrocardiograph 100 and the MRI apparatus 300 are connected with the ECG signal processing apparatus 1. The display 400 is connected with the ECG signal processing apparatus 1 as needed. The electrocardiograph 100 generates ECG signals, and time-sequentially transmits the generated ECG signals to the ECG signal processing apparatus 1. The ECG signal processing apparatus 1 sequentially generates synchronization signals from the respective ECG signals, and time-sequentially transmits the synchronization signals to the MRI apparatus 300.

The electrocardiograph 100 includes electrodes 101*a* and 101*b*, a differential amplifier 110, and an A/D (analogue to digital) converter 120. The electrodes 101*a* and 101*b* are attached to a human body. The differential amplifier 110 amplifies weak electric potential difference between the electrodes 101*a* and 101*b*. The A/D converter 120 samples the analogue signal amplified by the amplifier 110 at sampling intervals of, e.g., one millisecond so as to convert it into a digital signal.

Although two electrodes 101*a* and 101*b* are illustrated in FIG. 5, the number of electrodes of the electrocardiograph 100 is not limited to two. For example, in order to obtain a twelve-lead electrocardiogram, the electrocardiograph 100 may be configured to include four electrodes to be attached to the respective four limbs and further six electrodes to be attached to a chest. Additionally, instead of the method of obtaining electrical potential difference between two points of a body, a method of recording electrical potential difference between a reference determined in advance and an attached point of an electrode may be used.

The MRI apparatus 300 includes at least a gradient coil 310 and an MRI control circuit 320. The MRI control circuit 320 supplies the gradient coil 310 with gradient magnetic field currents so as to cause the gradient coil 310 to generate gradient magnetic fields. Additionally, the MRI control circuit 320 outputs gradient magnetic field signals, each of which has a waveform corresponding to each gradient magnetic field current, to the ECG signal processing apparatus 1. When the MRI apparatus 300 performs ECG synchronization imaging, the MRI apparatus 300 images an object by performing a pulse sequence synchronized with each heartbeat period with the use of each synchronization signal which is detected from each ECG signal by the ECG signal processing apparatus 1.

Additionally, the MRI apparatus 300 outputs an imaging period/non-imaging period signal indicating whether gradient pulses are currently applied or not (i.e., whether it is in an imaging period or in a non-imaging period) to the ECG signal processing apparatus 1. For example, the imaging period/non-imaging period signal may be a signal outputted from a gradient magnetic field power supply configured to generate the gradient magnetic field currents or may be a control signal outputted from a sequencer configured to control the gradient magnetic field power supply. Additionally or alternatively, the imaging period/non-imaging period signal may be a signal outputted from a console (i.e., a host computer) configured to control the entirety of the MRI apparatus 300.

As described above, the ECG signal processing apparatus 1 includes the processing circuitry 206 equipped with a processor. This processing circuitry 206 implements a function of an adaptive filter 10, a noise removal function 20, a detection function 30, a reference-parameter extraction function 40, and a reference-parameter storage function 50 shown in FIG. 5. The entire function of the adaptive filter 10 is composed of a noise estimation function 12, an error calculation function 14, a filter-coefficient update function 16, and a filter-coefficient storage function 18. These functions 12, 14, 16, and 18 are also implemented by the processing circuitry 206.

Here, the adaptive filter is a filter configured to update a filter coefficient in such a manner that an error between a previously determined reference value and a signal subjected to filtering becomes smaller. Since rigorous filter design in advance is not required as to an adaptive filter, operational burden on an operator is small. Further, since it is not necessary to attach special-purpose hardware to an examinee in the case of using an adaptive filter, burden on an examinee is small.

The noise estimation function 12 of the adaptive filter 10 can be achieved by, e.g., an FIR (Finite Impulse Response) filter of variable weight coefficient type.

Figure 6:
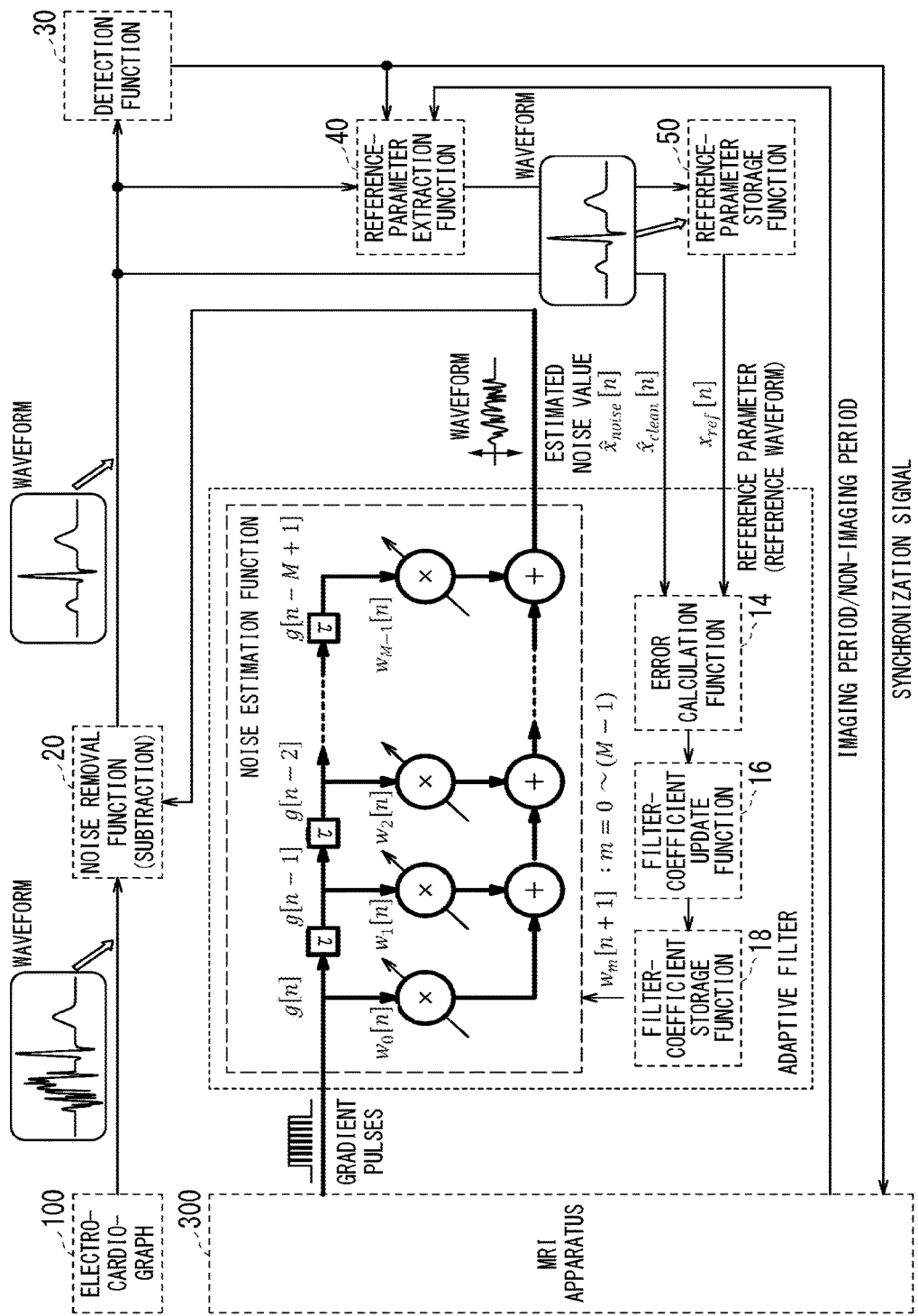
FIG. 6 is the second functional block diagram of the ECG signal processing apparatus according to the first embodiment.

FIG. 6 is the second functional block diagram of the ECG signal processing apparatus 1, illustrating a case of achieving the noise estimation function 12 shown in FIG. 5 by an FIR (Finite Impulse Response) filter of variable weight coefficient type whose tap length is M. In the FIR filter shown in FIG. 6, $g[n]$ indicates a gradient magnetic field signal at a time point n, and Z indicates a delay time. Additionally, $W_m[n]$ indicates a weight coefficient of tap number m at the time point n, where the tap number m is in the range of zero to M−1.

Figure 7:
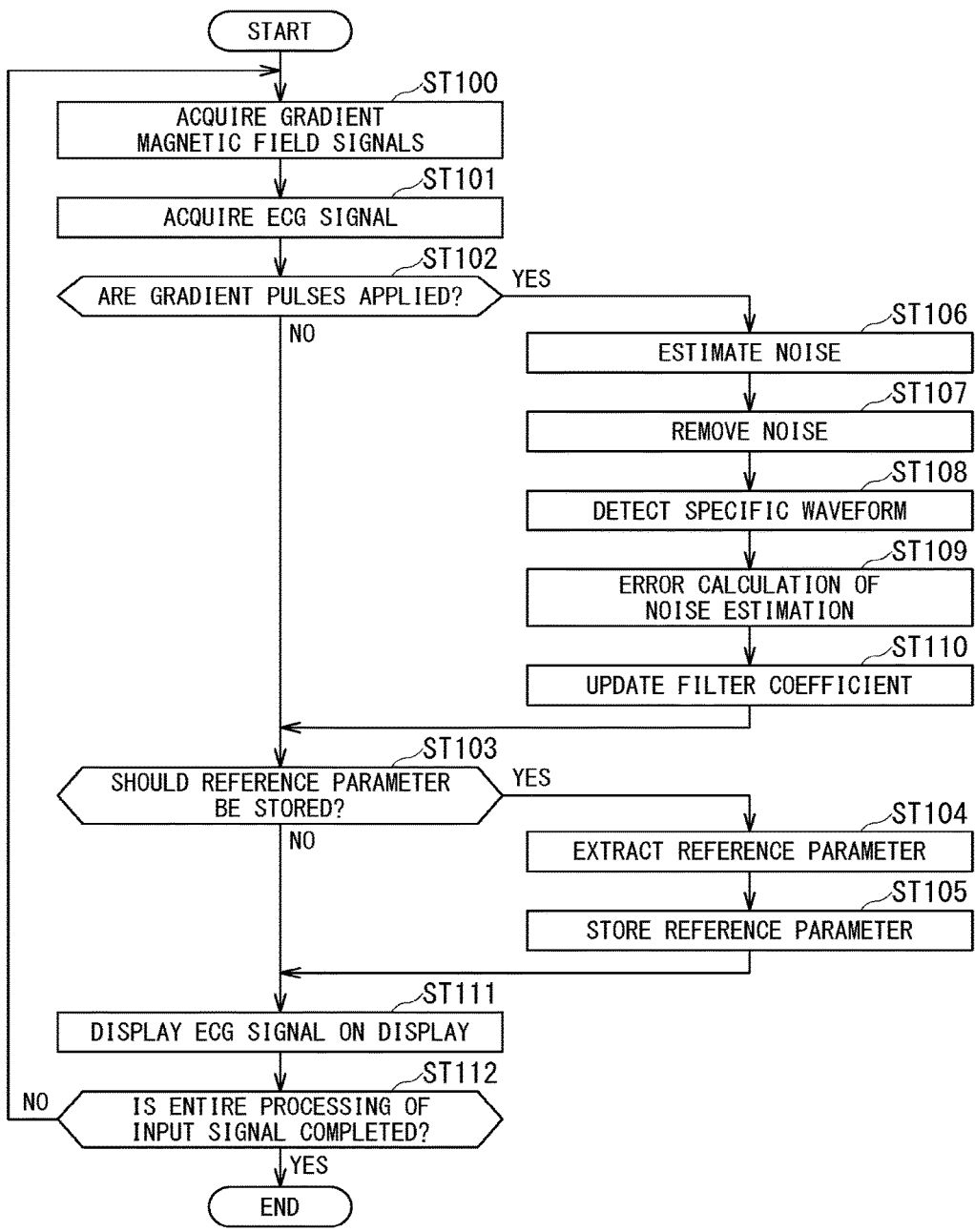
FIG. 7 is a flowchart illustrating processing performed by the ECG signal processing apparatus according to the first embodiment.

FIG. 7 is a flowchart illustrating processing performed by the ECG signal processing apparatus according to the first embodiment. Hereinafter, the respective functions shown in FIG. 5 and FIG. 6 will be described according to the step number shown in FIG. 7.

The step ST100 is processing corresponding to a part of the noise estimation function 12. The processing circuitry 206 acquires gradient magnetic field signals as time-sequential signals from the MRI control circuit 320 of the MRI apparatus 300 via the second input circuit 202 (see FIG. 4). The gradient magnetic field signals to be acquired are, for example, digital signals of three channels for generating the X-axis gradient magnetic field, the Y-axis gradient magnetic field, and the Z-axis gradient magnetic field. These gradient magnetic field signals may be digital signals of three channels respectively corresponding to a slice selection gradient magnetic field, a frequency encode gradient magnetic field, and a phase encode gradient magnetic field.

The step ST101 is processing corresponding to a part of the noise removal function 20. Note that the terms "noise removal", "noise removal function", "remove noise", and "noise removal processing" described below are used for meaning not only to completely eliminate noise but also to reduce or suppress noise.

The processing circuitry 206 acquires ECG signals as time-sequential signals from the A/D converter 120 of the electrocardiograph 100 via the first input circuit 201. The ECG signals to be acquired are digital signals sampled at, e.g., 1000 Hz (i.e., sampling period is one millisecond) by the A/D converter 120 of the electrocardiograph 100.

The steps ST102 to ST104 are processing mainly corresponding to the reference-parameter extraction function 40.

In the step ST102, the processing circuitry 206 acquires an operation signal (e.g., an imaging period/non-imaging period signal) indicating whether gradient pulses are currently applied or not from the MRI apparatus 300, and determines whether gradient pulses are currently applied by the MRI apparatus 300 or not. Instead of this operation or in addition to this operation, the processing circuitry 206 may monitor each gradient magnetic field signal acquired in the step ST100 and determine whether gradient pulses are currently applied or not based on presence/absence of the gradient magnetic field signal. When gradient pulses are not currently applied, the processing proceeds to the step ST103.

In the step ST103, the processing circuitry 206 determines whether a reference parameter should be extracted or not, i.e., whether a reference parameter should be extracted and stored or not. The processing circuitry 206 can determine that extraction of a reference parameter is permitted only in a period during which gradient pulses are not applied, on the basis of a signal indicating whether gradient pulses are currently applied or not in a manner similar to the step ST102.

As shown in FIG. 5 and FIG. 6, each ECG signal outputted from the noise removal function 20 is inputted to the reference-parameter extraction function 40. Hereinafter, each ECG signal outputted from the noise removal function 20 is referred to as "an ECG signal subjected to noise removal processing". In each period during which gradient pulses are not applied, noise is not superimposed on an ECG signal subjected to noise removal processing, regardless of noise removal processing has been performed on this ECG signal or not. In the step ST104, a reference parameter is extracted from this ECG signal subjected to noise removal processing.

Here, a reference parameter means a parameter indicative of characteristics of an ECG signal generated and outputted in a period during which gradient pulses are not applied. For example, a waveform of an ECG signal generated and outputted in a period during which gradient pulses are not applied can be treated as a reference parameter. In other words, a waveform (i.e., time-sequential data) of an ECG signal which changes depending only on cardiac action potential and on which noise attributable to gradient magnetic fields is not superimposed can be used for a reference parameter.

An R-wave can be comparatively easily detected by the detection function 30 shown in FIG. 5 and FIG. 6 from an ECG signal when gradient pulses are not applied. For this reason, when a waveform of an ECG signal is used for a reference parameter, the extraction range of an ECG signal can be determined based on the position of the detected R-wave on the time axis. For example, the past period ending at the detection time of an R-wave and having predetermined length and/or a period of predetermined length before and after the arrival timing of an R-wave may be extracted from an ECG signal subjected to noise removal processing, so that the extracted waveform of an ECG signal is used for a reference parameter.

Aside from the above-described periods, a peak value of an R-wave in a period during which gradient pulses are not applied and/or average electric power of an ECG signal in a period during which gradient pulses are not applied may also be used for a reference parameter.

Additionally, a combination of the above-described options such as a combination of an extracted waveform of an ECG signal and a peak value of an R-wave and a combination of an extracted waveform of an ECG signal and the above-described average electric power of an ECG signal may also be used for a reference parameter.

The step ST105 is processing corresponding to the reference-parameter storage function 50. The processing circuitry 206 stores the reference parameter extracted in the step ST104 in the memory circuitry 203. The memory circuitry 203 may hold one or more reference parameters.

Additionally, in the steps ST104 and ST105, the processing circuitry 206 may sequentially extract a reference parameter from each ECG signal subjected to noise removal processing in a non-imaging period (i.e., a period during which gradient pulses are not applied) so as to sequentially update the reference parameter stored in the memory circuitry 203 by using the extracted reference parameter.

The waveform illustrated in the lower right part of FIG. 6 is a schematic waveform of an ECG signal (on which noise is not superimposed) stored as a reference parameter in the memory circuitry 203 by the reference-parameter storage function 50.

Meanwhile, when it is determined in the step ST102 that gradient pulses are currently applied (i.e., it is in an imaging period), the processing proceeds to the step ST106.

The step ST106 is processing corresponding to the noise estimation function 12. As described above, the noise estimation function 12 can be realized by, e.g., an FIR filter of variable filter coefficient type whose tap length is M as illustrated in FIG. 6. The input to this FIR filter is gradient magnetic field signals and the output of this FIR filter is an estimated value of noise superimposed on an ECG signal.

Here, when a time point is defined as n and an estimated value of noise at a time point n is defined as $\hat{x}_{noise}[n]$, the estimated value of noise can be expressed by the following formula (1).

$$\hat{x}_{noise}[n] = \sum_{m=0}^{M-1} w_m[n](g_x[n-m] + g_y[n-m] + g_z[n-m]) \quad \text{Formula (1)}$$

In the formula (1), $w_m[n]$ indicates a filter coefficient for the tap number m (m=0 to M−1) at time point n. Additionally, $g_x[n-m]$, $g_y[n-m]$, $g=[n-m]$ indicate respective gradient magnetic field signals in the triaxial directions orthogonal to each other (i.e., the X-axis, the Y-axis, and the Z-axis) inputted to the tap whose number is m at the time point n.

In the formula (1), an estimated value of noise is determined by summing three gradient magnetic field signals in the respective triaxial directions and inputting the summed signal to the FIR filter. In the FIR filter shown in FIG. 6, the summed signal of the three gradient magnetic field signals in the respective triaxial directions is indicated as g[n−m].

Additionally or alternatively, the three gradient magnetic field signals in the triaxial directions orthogonal to each other (i.e., the X-axis, the Y-axis, and the Z-axis) may be separately inputted to three FIR filters so that outputs of these three FIR filters are summed up and this summation is treated as an estimated value of noise. In this case, an estimated value of noise can be expressed by the following formula (2).

$$\hat{x}_{noise}[n] = \sum_{m=0}^{M-1} w_{x,m}[n]g_x[n-m] + \sum_{m=0}^{M-1} w_{y,m}[n]g_y[n-m] + \sum_{m=0}^{M-1} w_{z,m}[n]g_z[n-m]$$ Formula (2)

In the step ST106, the processing circuitry 206 estimates noise superimposed on an ECG signal by computing the above-described formula (1) or formula (2), with the use of the filter coefficients $w_m[n]$ stored in the memory circuitry 203 and the gradient magnetic field signals $g_x[n-m]$, $g_y[n-m]$, and $g_z[n-m]$ acquired in the step ST100.

The next step ST107 is processing corresponding to the noise removal function 20. In the step ST107, the processing circuitry 206 performs noise removal processing on the ECG signal acquired in the step ST101. Specifically, as indicated by the following formula (3), the processing circuitry 206 determines an ECG signal subjected to noise removal processing by subtracting the estimated value of noise determined in the step ST106 from the ECG signal acquired in the step ST101.

$$\hat{x}_{clean}[n] = x_{ecg}[n] - \hat{x}_{noise}[n]$$ Formula (3)

Here, $\hat{x}_{clean}[n]$ is an ECG signal subjected to noise removal processing at a time point n, and $x_{ecg}[n]$ is an ECG signal at a time point n before noise removal processing.

The step ST108 is processing corresponding to the detection function 30. In the step ST108, the processing circuitry 206 detects a specific waveform from the ECG signal subjected to noise removal processing. Specifically, the processing circuitry 206 detects an R-wave. Detection of n R-wave may be performed by, e.g., comparing a previously determined threshold value with an amplitude value of the ECG signal subjected to noise removal processing. Detection of n R-wave may be performed by performing pattern matching between an R-wave template prepared in advance and the ECG signal subjected to noise removal processing.

The step ST109 is processing corresponding to the error calculation function 14. In the step ST109, the processing circuitry 206 calculates an error between the reference parameter (i.e., the first parameter) stored in the step ST105 and the parameter (i.e., the second parameter) extracted from the ECG signal subjected to noise removal processing. The first parameter and the second parameter used for calculating the error correspond to each other. For example, when a reference parameter is an ECG waveform in a period during which gradient pulses are not applied, the second parameter is an ECG waveform extracted from the ECG signal subjected to noise removal processing in a period during which gradient pulses are applied. As an error, the least mean square error $\varepsilon_{LMS}$ indicated by the following formula (4) can be used.

$$\varepsilon_{LMS}[n] = (x_{ref}[n] - \hat{x}_{clean}[n])^2$$ Formula (4)

Here, $\varepsilon_{LMS}[n]$ is the least mean square error at a time point n, and $x_{ref}[n]$ is a reference parameter corresponding to a time point n (i.e., a waveform of an ECG signal acquired when gradient pulses are not applied). An absolute difference value (i.e., an L1 norm) may be used as an error aside from the above least mean square error.

The step ST110 is processing corresponding to the filter-coefficient update function 16. In the step ST110, the processing circuitry 206 calculates a filter update amount $\Delta w_m[n]$ for reducing the calculated error. Then, the weight coefficient stored in the memory circuitry 203 is updated by calculating the weight coefficient $w_m[n+1]$ at the next time point n+1 under the following formula (5) with the use of the weight coefficient $w_m[n]$ at the current time point n stored in the memory circuitry 203 and the calculated filter update amount $\Delta w_m[n]$ $$w_m[n+1] = w_m[n] + \Delta w_m[n] \text{ wherein } m=0 \text{ to } M-1$$ Formula (5)

When the least mean square error is used as an error, the filter update amount $\Delta w_m[n]$ can be calculated by the following formula (6).

$$\Delta w_m[n] = -2 \mu g[n-m](x_{ref}[n] - \hat{x}_{clean}[n])$$ Formula (6)

The formula (6) corresponds to the formula (1), and $g[n-m]$ in the formula (6) is a sum signal of three gradient magnetic field signals in the triaxial directions orthogonal to each other. Additionally, $\mu$ is a parameter referred to as a step size and can be designed in advance by, e.g., computation simulation.

The processing from the steps ST106 to ST110 is processing repeated per time point n. Out of the respective parts of the processing from the steps ST106 to ST110, the steps ST106, ST107, ST109, and ST110 substantially correspond to processing performed by the adaptive filter 10.

In the step ST111, a waveform of an ECG signal subjected to noise removal processing is displayed on the display 400 (FIG. 5), as needed.

The step ST112 is processing of determining whether the entire processing is completed or not, and the processing from the steps ST100 to ST111 is repeated until a command to complete the entire processing is inputted from outside.

Figure 8:
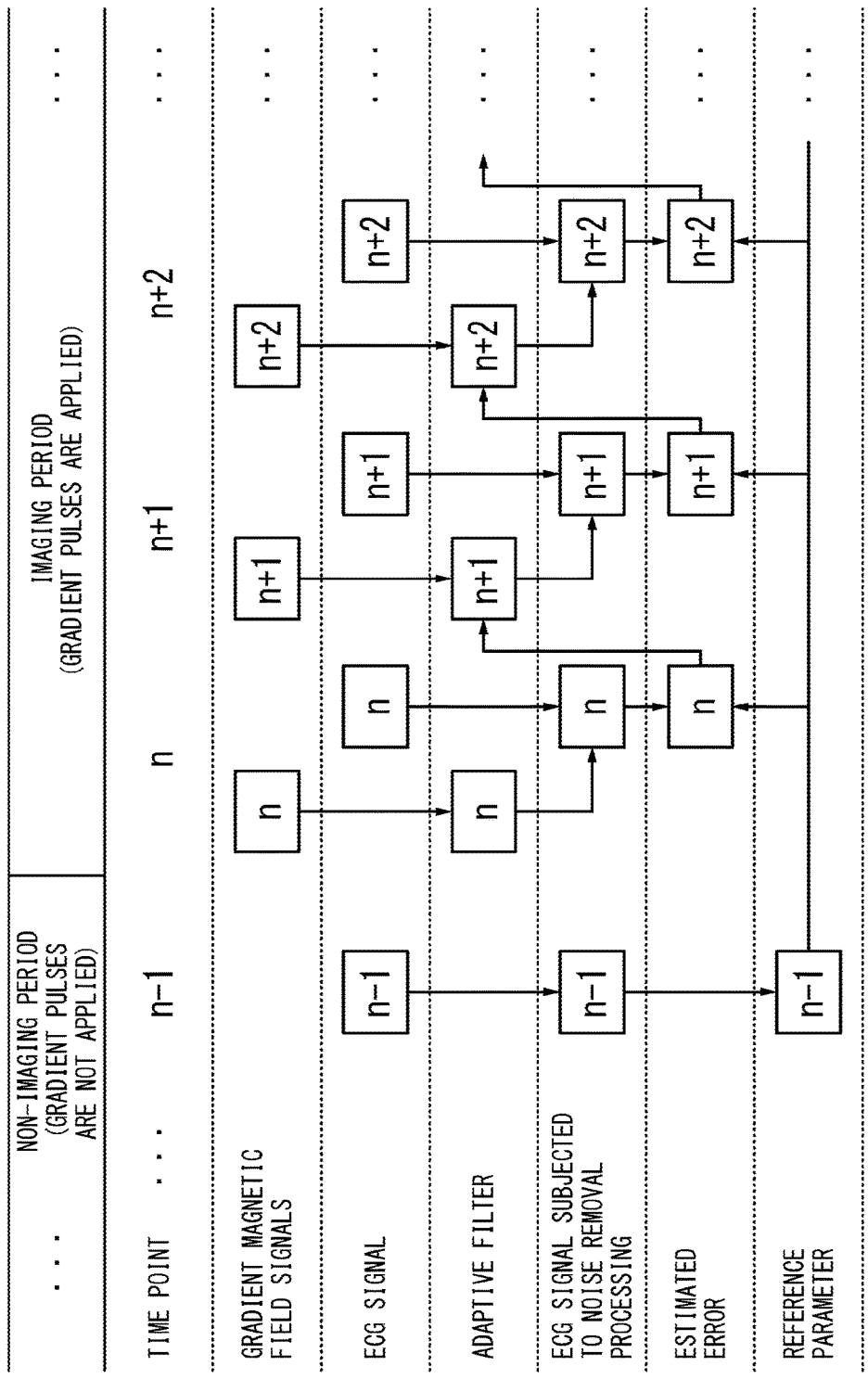
FIG. 8 is a schematic diagram illustrating a flow of data and processing drawn in such a manner that its horizontal direction corresponds to the direction of each point in time and respective arrows in the vertical direction indicate transmission of data between the steps in FIG. 7.

FIG. 8 is schematic diagram illustrating a flow of data and a flow of processing drawn in such a manner that its horizontal direction corresponds to the direction of each point in time and respective arrows along the vertical direction indicate transmission of data between the above-described steps in FIG. 7.

As described above, the adaptive filter 10 updates the filter coefficient so as to reduce the error $\varepsilon_{LMS}[n]$, i.e., so as to bring the error $\varepsilon_{LMS}[n]$ close to zero. In other words, the adaptive filter 10 updates the filter coefficient so as to enhance similarity between an ECG signal acquired in a period during which gradient pulses are not applied and an ECG signal subjected to noise removal processing under the condition that gradient pulses are applied. Thus, in the ideal condition where the filter coefficient has converged, an ECG signal subjected to noise removal processing under the condition that gradient pulses are applied approximately matches an ECG signal acquired in a period during which gradient pulses are not applied.

From another point of view, in the ideal condition where the filter coefficient has converged, an estimated value of noise outputted from an FIR filter approximately matches noise superimposed on an ECG signal due to gradient pulses. As the result, superimposed noise is removed from an ECG signal subjected to noise removal processing which is obtained by subtracting an estimated value of noise from an ECG signal before noise removal processing, and accordingly, an ECG signal which changes depending only on cardiac action potential can be obtained.

FIG. 9A to FIG. 9C are graphs illustrating temporal change of ECG signals, which indicate advantageous effects of the ECG signal processing apparatus 1 according to the first embodiment. A volunteer has undergone an MRI examination, and to what extent cardiac action potential can be kept undisturbed while removing noise except action potential is evaluated by using the ECG signals and the gradient magnetic field signals recorded during the MRI examination. In the ECG signal, i.e., the input signal inputted to the ECG signal processing apparatus 1 shown in FIG. 9A, noise attributable to an RF pulse is mixed approximately at the midpoint of two successive R-waves, and noise attributable to gradient pulses is mixed at a short span immediately before arrival of each R-wave.

FIG. 9B illustrates an ECG signal subjected to noise removal processing of a conventional method based on an adaptive filter without using a reference parameter. This conventional method is disclosed in the following Non-patent document 1, for example.

[Non-patent Document 1] "Suppression of MR gradient artefacts on electrophysiological signals based on an adaptive real-time filter with LMS coefficient updates", R. Abacherli, et al., MAGMA, 18:41-50, 2005.

In the conventional method, though noise removal amount is large, effects of noise removal is excessive. Thus, in the conventional method, each P-wave and each T-wave indicating cardiac action potential are also removed, and the resultant ECG wave lacks most information of the cardiac action potential. Additionally, in the conventional method, amplitude of each R-wave is made smaller than the input signal and it can be understood that the cardiac action potential is reduced in whole.

FIG. 9C illustrates the ECG signal subjected to noise removal processing in accordance with the processing method of the ECG signal processing apparatus 1 of the first embodiment. As is clear from FIG. 9C, according to the ECG signal processing apparatus 1 of the first embodiment, noise caused by RF pulses and gradient pulses is almost completely removed while the cardiac action potential such as each P-wave, each T-wave, and each R-wave is kept undisturbed.

As described above, according to the ECG signal processing apparatus 1 of the first embodiment, noise caused by gradient magnetic fields and superimposed on an ECG signal is suppressed and characteristics of cardiac action potential can be stably and accurately extracted. As a result, even in a period during which imaging is performed by the MRI apparatus, each synchronization signal can be stably and infallibly supplied to the MRI apparatus.

Second Embodiment

The second embodiment of the ECG signal processing apparatus 1 performs the noise estimation processing and the noise removal processing in a frequency domain. The same reference numbers are assigned to the same components and processing as the first embodiment and duplicate description is omitted.

Figure 10:
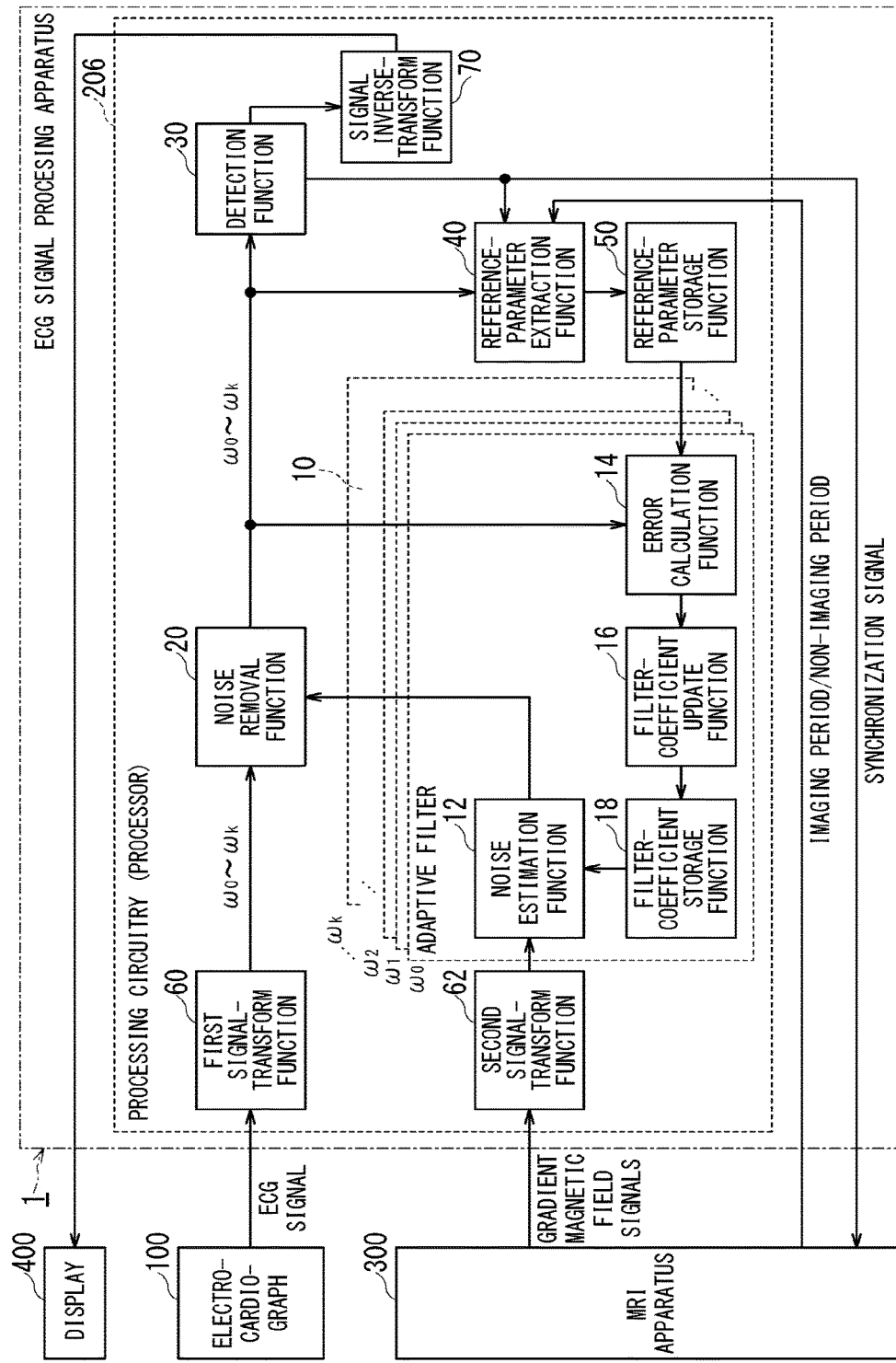
FIG. 10 is a block diagram illustrating configuration of the ECG signal processing apparatus according to the second embodiment.

FIG. 10 is a block diagram illustrating functional configuration of the ECG signal processing apparatus 1 according to the second embodiment. In the second embodiment, the processing circuitry 206 implements a first signal-transform function 60, a second signal-transform function 62, and a signal inverse-transform function 70 in addition to the functions included in the first embodiment.

The first signal-transform function 60 buffers each ECG signal acquired from the electrocardiograph 100, and transforms it into a frequency domain. The first signal-transform function 60 can store, e.g., ECG signals of the latest 256 samples, and transforms the ECG signals of the latest 256 samples into a frequency domain. Hereinafter, an ECG signal transformed into a frequency domain is referred to as an ECG spectrum.

The second signal-transform function 62 buffers gradient magnetic field signals acquired from the MRI apparatus 300, and transforms the gradient magnetic field signals into a frequency domain. Hereinafter, a gradient magnetic field signal transformed into a frequency domain is referred to as a gradient magnetic field spectrum. The second signal-transform function 62 can store, e.g., gradient magnetic field signals of the latest 256 samples, and transforms the gradient magnetic field signals of the latest 256 samples into a frequency domain, in a manner similar to the first signal-transform function 60.

Additionally, the noise removal function 20, the detection function 30, the reference-parameter extraction function 40, the reference-parameter storage function 50, and the respective functions of the adaptive filter 10 are performed for each frequency band of a transformed spectrum expressed in a frequency domain. Note that the processing of each of the above-described functions in each frequency band is substantially the same as the first embodiment.

The noise estimation function 12 acquires a gradient magnetic field spectrum from the second signal-transform function 62. When gradient pulses are applied, the noise estimation function 12 estimates noise mixed into an ECG signal due to the gradient pulses by using the filter coefficient stored in the memory circuitry 203. This estimation of noise is performed by, e.g., using the following formula (7).

$$|\hat{x}_{noise,\omega}[n]| = \sum_{m=0}^{M-1} w_{m,\omega}[n](|G_{x,\omega}[n-m]| + |G_{y,\omega}[n-m]| + |G_{z,\omega}[n-m]|) \quad \text{Formula (7)}$$

Here, $|\hat{X}_{noise,\omega}[n]|$ is an estimated value of a power spectrum of noise at a time point n in a frequency band ω.

Similarly, $|G_{x,\omega}[n-m]|$, $|G_{y,\omega}[n-m]|$, and $|G_{z,\omega}[n-m]|$ indicate respective power spectrums of three gradient magnetic field signals.

The formula (7) corresponds to a processing, which applies one adaptive filter to a sum value of power spectrums of three gradient magnetic field signals in the triaxial directions orthogonal to each other (i.e., the sum of three gradient magnetic field spectrums).

As a modification, three adaptive filters may be separately applied to the respective power spectrums of the three gradient magnetic field signals in the triaxial directions, so that a sum value of the outputs of the three adaptive filters is determined as an estimated value of a power spectrum of noise in a manner similar to the first embodiment. In this case, an estimated value of a power spectrum of noise can be calculated by the following formula (8).

$$|\hat{x}_{noise,\omega}[n]| = \sum_{m=0}^{M-1} w_{x,m,\omega}|G_{x,\omega}[n-m]| + \quad \text{Formula (8)}$$

-continued $$\sum_{m=0}^{M-1} w_{y,m,\omega}|G_{y,\omega}[n-m]| + \sum_{m=0}^{M-1} w_{z,m,\omega}|G_{z,\omega}[n-m]|$$

Here, $w_{x,m,\omega}[n]$, $w_{y,m,\omega}[n]$, and $w_{z,m,\omega}[n]$ indicate filter coefficients of the respective adaptive filters.

The noise removal function 20 acquires an ECG spectrum from the first signal-transform function 60, and removes the noise estimated by the noise estimation function 12. For example, in noise removing processing by the noise removal function 20, spectrum subtraction ($H_{ss,\omega}[n]$) based on the following formula (9) and/or the wiener filter ($H_{wf,\omega}[n]$) based on the following formula (10) may be used.

$$H_{ss,\omega}[n] = 1 - \frac{|\hat{X}_{noise,\omega}[n]|}{|X_{ecg,\omega}[n]|} \quad \text{Formula (9)}$$

$$H_{wf,\omega}[n] = \frac{|X_{ecg,\omega}[n]|^2 - |\hat{X}_{noise,\omega}[n]|^2}{|X_{ecg,\omega}[n]|^2} \quad \text{Formula (10)}$$

Here, $X_{ecg,\omega}[n]$ is a power spectrum of an ECG signal before the noise removal processing. By multiplying one of the filters of formulas (9) and (10) to an ECG signal before the noise removal processing, a spectrum ($\hat{X}_{clean,\omega}[n]$) of an ECG signal subjected to noise removal processing is obtained.

As to phase information, a phase of an ECG signal acquired from the first signal-transform function 60 can be directly treated as a phase of an ECG signal subjected to noise removal processing.

The reference-parameter extraction function 40 receives an ECG spectrum subjected to noise removal processing acquired from the noise removal function 20, determines whether a reference parameter should be extracted or not, and extracts a reference parameter in the case of an affirmative determination result. Whether a reference parameter should be extracted or not may be determined depending on, e.g., whether the current time point is in an R-wave span or not.

As a reference parameter, for example, a power spectrum of an ECG signal subjected to noise removal processing acquired in a period during which gradient pulses are not applied may be used. Additionally, a reference parameter may be extracted at a time point ($n_R$) when a peak of an R-wave is detected by the detection function 30, as shown in the following formula (11).

$$|X_{ref,\omega}| = |X_{clean,\omega}[n_R]| \quad \text{Formula (11)}$$

Alternatively, as shown in the following formula (12), the average power spectrum in a predetermined period (from $n_0$ to $n_1$) may be extracted. This predetermined period is, for example, an average period of one heartbeat.

$$|X_{ref,\omega}| = \frac{1}{n_1 - n_0}\sum_{n=n_0+1}^{n_1} |X_{clean,\omega}[n]| \quad \text{Formula (12)}$$

Aside from the above methods, a combination of a reference parameter extracted in a period of an R-wave and another reference parameter extracted in a period excluding a period of each R-wave may be used.

The error calculation function 14 calculates an error from the stored reference parameter (i.e., the first parameter which is a power spectrum of an ECG signal acquired in a period during which gradient pulses are not applied) and the second parameter (i.e., a power spectrum of an ECG signal subjected to noise removal processing in a period during which gradient pulses are applied). In the calculation of an error, for example, the following formula (13) may be used as a mean square error for each frequency band.

$$\varepsilon_{LMS,\omega}[n] = (X_{ref,\omega}[n] - \hat{X}_{clean,\omega}[n])^2 \quad \text{Formula (13)}$$

Here, $X_{ref,\omega}[n]$ is a reference parameter expressed by a power spectrum of each frequency band. Aside from the formula (13), an L1 norm of an absolute difference value may be used for calculating an error.

The filter-coefficient update function 16 calculates filter update amount for reducing the calculated error, and updates the filter coefficient stored in the memory circuitry 203. For example, when a mean square error is used for an error, the update processing can be performed by calculating the following formulas (14) and (15).

$$w_{m,\omega}[n+1] = w_{m,\omega}[n] + \Delta w_{m,\omega}[n] \quad \text{(Formula 14)}$$

$$\Delta w_{m,\omega}[n] = -2\mu_\omega G_\omega[n-m](X_{ref,\omega}[n] - \hat{X}_{clean,\omega}[n]) \quad \text{(Formula 15)}$$

Here, $\mu_\omega$ is a parameter referred to as a step size, and can be set to a value which is different for each frequency band. The step size $\mu_\omega$ can be designed in advance by computation simulation.

The filter storage function 18 stores the filter coefficient determined by the formulas (14) and (15) for each frequency band of each gradient magnetic field signal expressed by a frequency domain.

Figure 11:
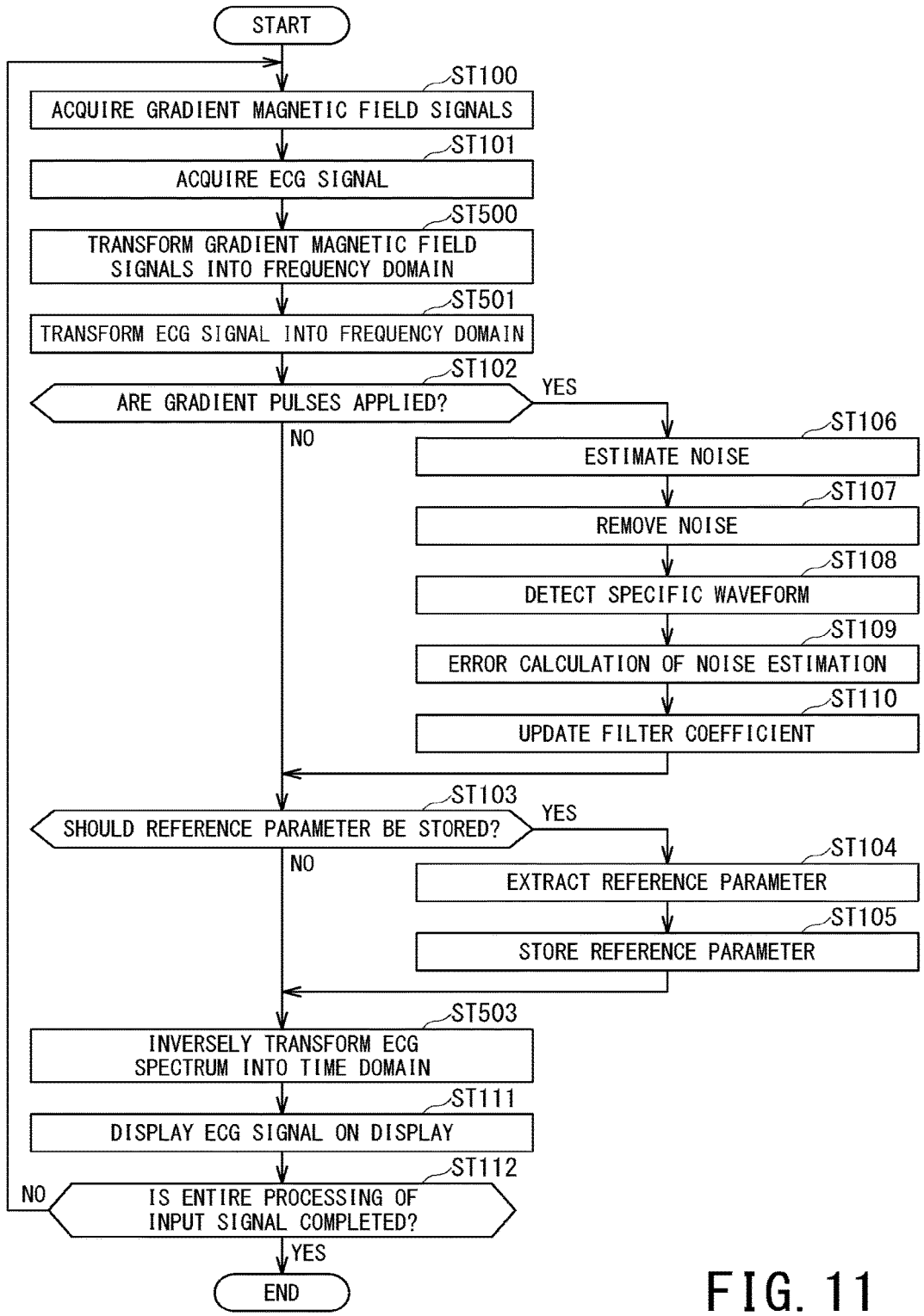
FIG. 11 is a flowchart illustrating processing performed by the ECG signal processing apparatus of the second embodiment.

FIG. 11 is a flowchart illustrating processing performed by the ECG signal processing apparatus 1 of the second embodiment. In the second embodiment, STFT (Short-Term Fourier Transform) is performed, then noise estimation, noise removal, R-wave detection, reference-parameter extraction, filter update are performed in a frequency domain, and then inverse Fourier transform is performed on each ECG signal subjected to noise removal processing. Since processing from the steps ST100 to ST112 is similar to the first embodiment, duplicate description is omitted.

In the step ST500, the second signal-transform function 62 transforms time-sequential gradient magnetic field signals acquired in the step ST100 together with the past gradient magnetic field signals stored in the buffer into a frequency domain. A window function such as a hamming window or a hanning window may be multiplied to those gradient magnetic field signals before transforming into a frequency domain. The gradient magnetic field signals which are multiplied by a window function are transformed into power spectrums of gradient magnetic field signals (i.e., gradient magnetic field spectrum) by FET (Fast Fourier Transform).

Similarly, in the step ST501, the first signal-transform function 60 transforms time-sequential ECG signals acquired in the step ST101 together with the past ECG signals stored in the buffer into a frequency domain. A window function also may be multiplied to those ECG signals before being transformed in a manner similar to the step ST500.

In the step ST503, the signal inverse-transform function 70 receives spectrums of ECG signals subjected to noise removal processing performed by the noise removal function 20, and performs inverse FFT (Fast Fourier Transform) on the received spectrums of ECG signals so as to transform these spectrums into signals of a time domain. Incidentally, an overlap-add method may be applied to the inversely transformed signal by multiplying a window function used in the step ST500 or ST501 to the inversely transformed signal again. As to the application of the above-described overlap-add method, a window function different from the one used in the step ST500 or ST501 may be multiplied to the inversely transformed signal.

FIG. 12A and FIG. 12B are graphs illustrating temporal change of ECG signals, which indicate advantageous effects of the ECG signal processing apparatus 1 of the second embodiment, which is configured to perform noise removal on each ECG signal in a frequency domain. The ECG signal (input) in FIG. 12A is the same ECG signal as the ECG signal in FIG. 9A described in the first embodiment. Since adaptive filters are provided for respective frequency bands in a frequency domain in the second embodiment, the step size $\mu_\omega$ can be designed for each frequency band. For example, for a frequency band including a large part of spectrum of the cardiac action potential, adaptation rate is set to be slower, or the filter coefficient may be set so as not to be updated. On the other hand, for a frequency band in which a small part of spectrum or no spectrum of cardiac action potential is included, adaptation rate is set to be faster. As the result, in a frequency band in which a large part of spectrum of the action potential such as an R-wave and a T-wave is included, such action potential is held, not being suppressed. On the other hand, in a frequency band in which a small part of spectrum or no spectrum of the action potential is included, noise superimposed due to gradient pulses can be significantly suppressed.

As described above, according to the ECG signal processing apparatus 1 of the second embodiment, the same effects as the first embodiment can be obtained. In addition, in the second embodiment, degree of freedom for designing a step size is enhanced, because the step size can be independently optimized for each of frequency bands. Thus, it is easier to adjust the trade-off between maintaining the cardiac action potential and removal of the noise and to appropriately customize the entire system. FIG. 12B illustrates an ECG signal subjected to noise removal processing in the second embodiment. As is clear from FIG. 12B, noise generated from the MRI apparatus is removed, while the shape of each R-wave and each T-wave as cardiac action potential is kept undisturbed.

Modification of Second Embodiment

In the ECG signal processing apparatus 1 of the modification of the second embodiment, while noise estimation, noise removal, reference-parameter extraction, error calculation, and filter-coefficient update are performed in a frequency domain, detection of each R-wave is performed in a time domain after inversely transforming the ECG signal subjected to noise removal processing in the frequency domain.

Figure 13:
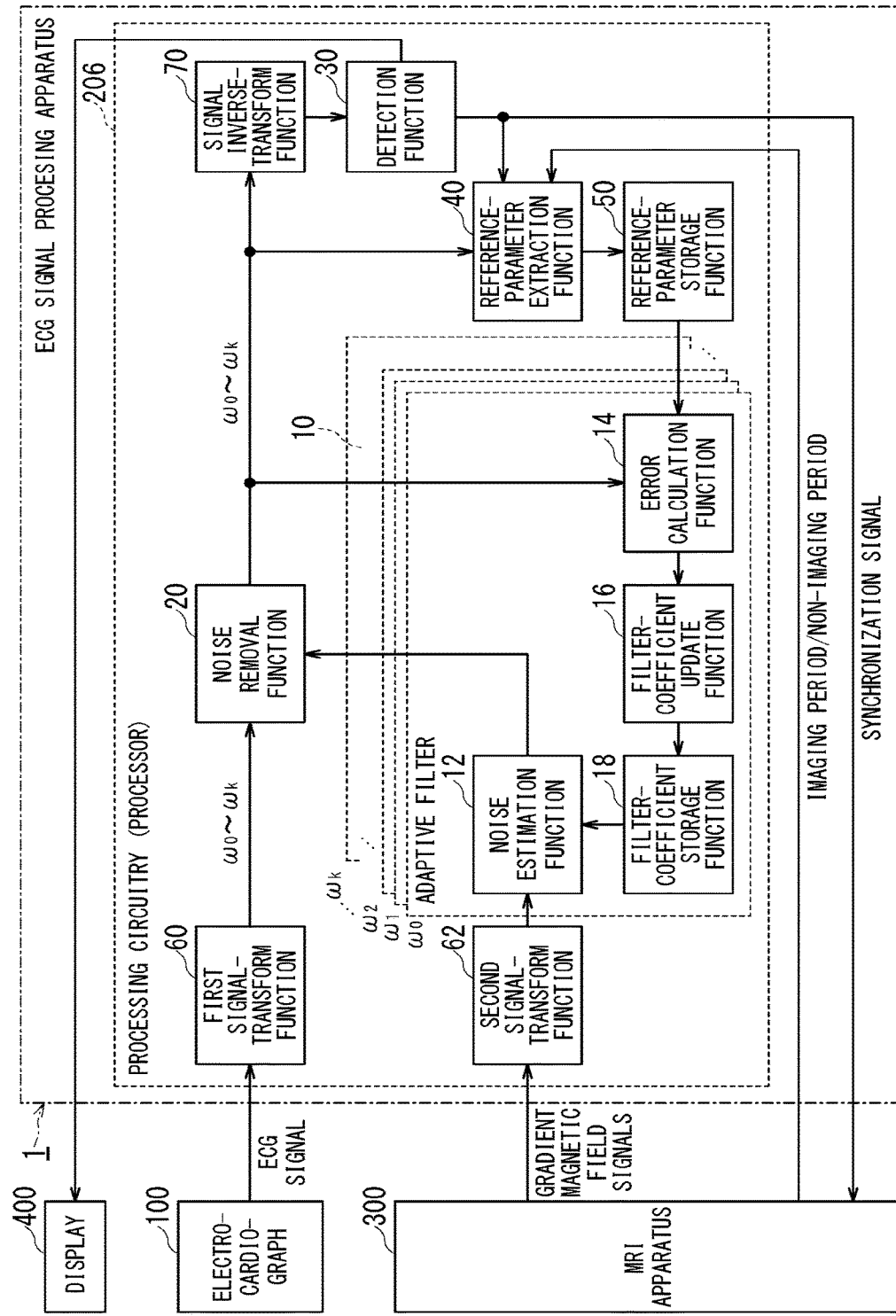
FIG. 13 is a block diagram illustrating configuration of an ECG signal processing apparatus in a modification of the second embodiment.

FIG. 13 is a block diagram illustrating functional configuration of the ECG signal processing apparatus 1 in the modification of the second embodiment. Although the detection function 30 receives output of the noise removal function 20 in the second embodiment (FIG. 10), the ECG signal processing apparatus 1 in the modification of the second embodiment is configured so that the detection function 30 receives output of the signal inverse-transform function 70.

Figure 14:
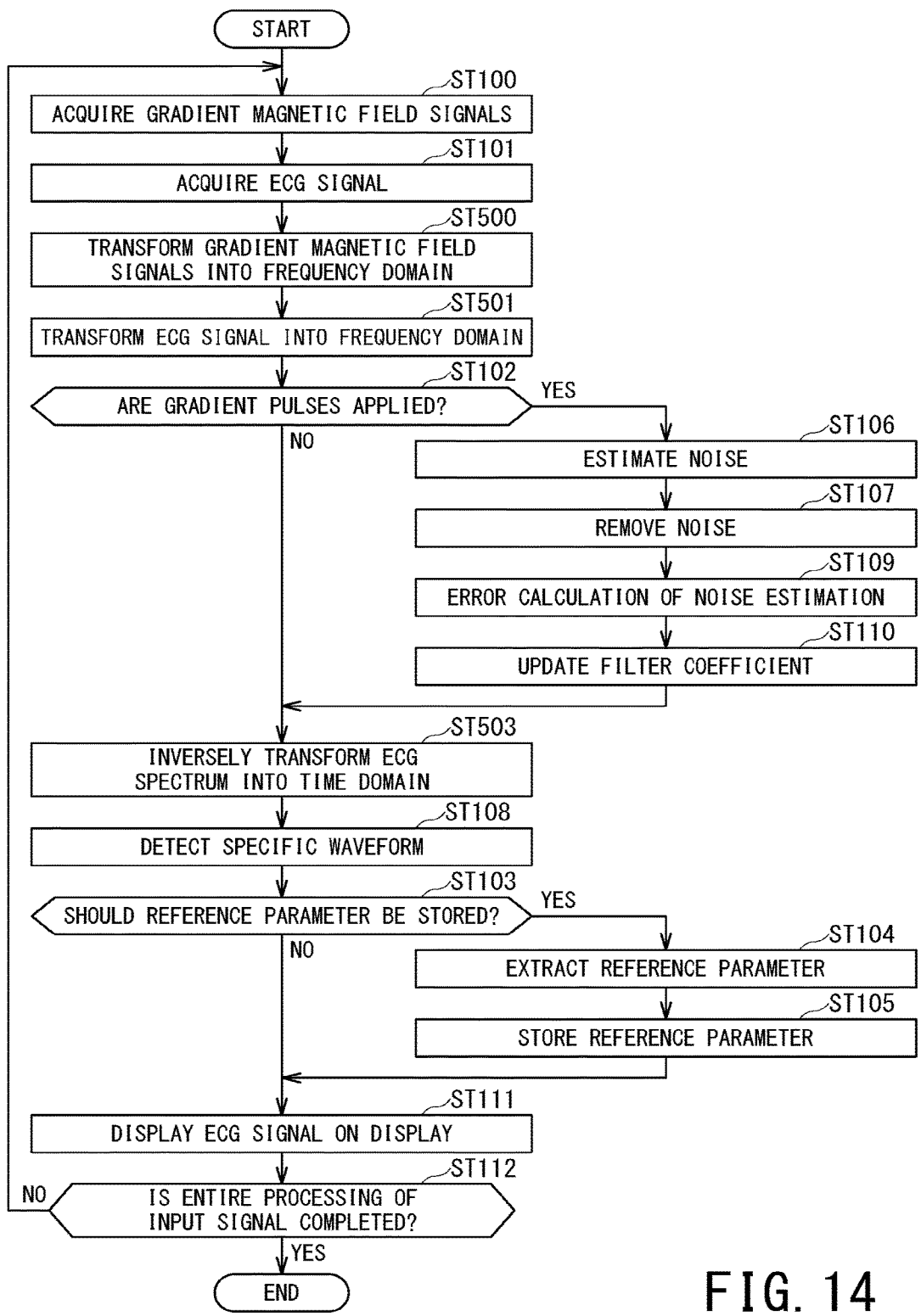
FIG. 14 is a flowchart illustrating processing performed by the ECG signal processing apparatus of the modification of the second embodiment.

FIG. 14 is a flowchart illustrating processing performed by the ECG signal processing apparatus 1 of the modification of the second embodiment.

In the modification of the second embodiment, processing of the step ST503, in which each ECG signal subjected to noise removal processing in a frequency domain is inversely transformed into a time domain, is executed prior to processing of the step ST108 in which a specific waveform (e.g., an R-wave) is detected.

In the step ST108, each R-wave is detected from each ECG signal subjected to noise removal processing expressed in a time domain.

Alternatively, the detection of the R-wave may be performed by using both of an ECG signal subjected to noise removal processing in a time domain and an ECG signal subjected to noise removal processing in a frequency domain in the step ST108.

Note that, regardless of the processing of the step ST108, the processing of the step ST104 and the step ST105 is executed by using each ECG signal in a frequency domain in a manner similar to the second embodiment.

MRI Apparatus

Figure 15:
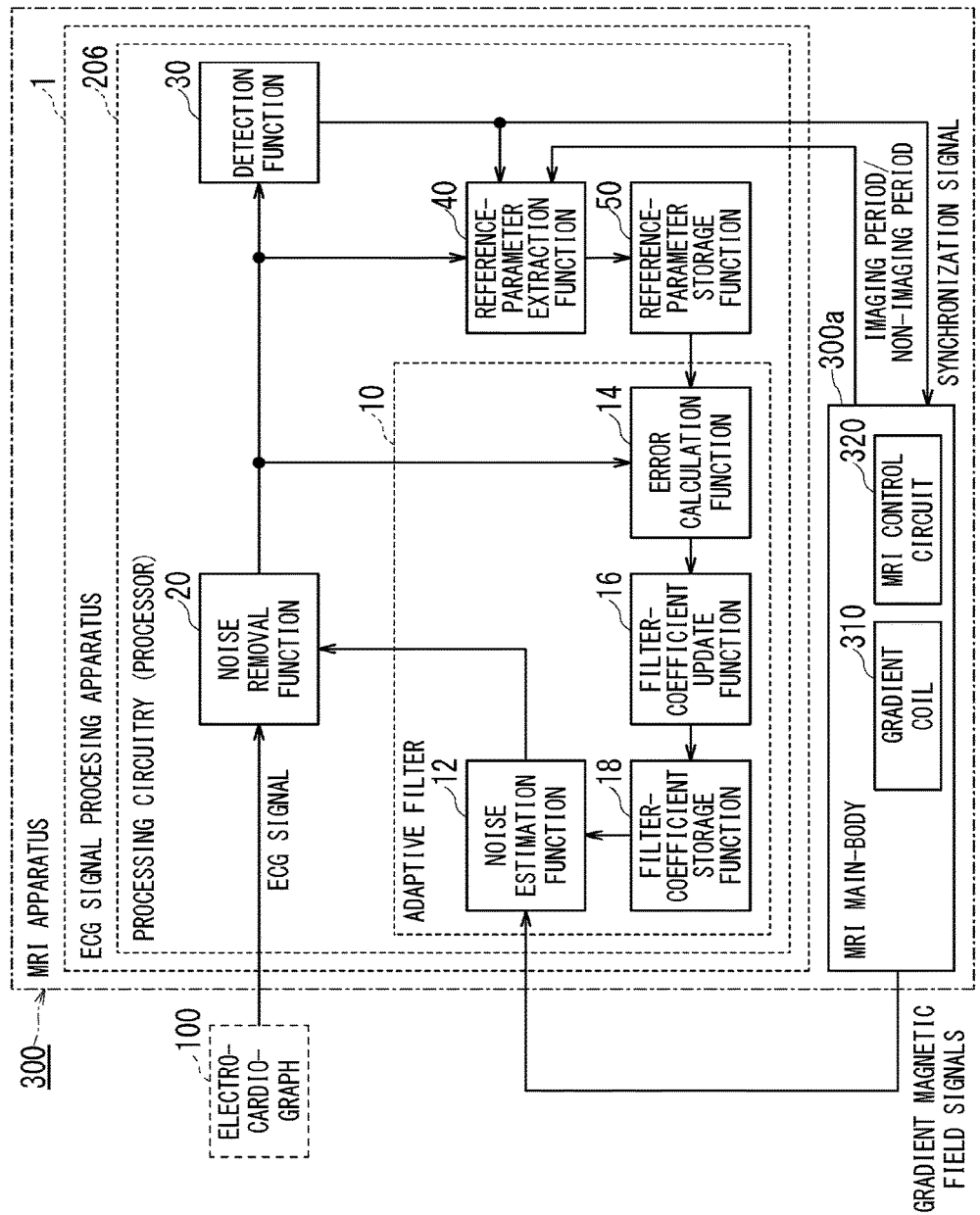
FIG. 15 is a block diagram illustrating configuration of an MRI apparatus in which the ECG signal processing apparatus of one of the embodiments is included.

FIG. 15 is a block diagram illustrating configuration of an MRI apparatus in which the ECG signal processing apparatus of one of possible embodiments is included. The MRI apparatus 300 includes an MRI main-body 300*a* configured to acquire imaging data from an object in synchronization with each synchronization signal and generate images of the object from the acquired imaging data, in addition to the ECG signal processing apparatus 1 configured to generate synchronization signals. The MRI main-body 300*a* includes at least a gradient coil 310 and an MRI control circuit 320.

Note that, in each of the above-described embodiments, the ECG signal processing apparatus 1 is configured so as to be separate from the electrocardiograph 100. However, this is only one aspect of possible embodiments, and the electrocardiograph 100 may be configured as an internal component of the ECG signal processing apparatus 1.

According to the ECG signal processing apparatus, the MRI apparatus, and the ECG signal processing method of at least one of the above-described embodiments, noise which is caused by gradient magnetic fields and then superimposed on an ECG signal can be suppressed.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ECG signal processing apparatus configured to be connected with an electrocardiograph and an MRI apparatus, the ECG signal apparatus comprising:
    memory circuitry; and
    processing circuitry configured to
        store a parameter of an ECG signal as a first parameter in the memory circuitry, the ECG signal being acquired from the electrocardiograph operating in combination with the MRI apparatus in a period during which a gradient pulse is not applied by the MRI apparatus,
        implement an adaptive filter for estimating noise mixed into the ECG signal due to the gradient pulse, by using the first parameter stored in the memory circuitry and a gradient magnetic field signal acquired from the MRI apparatus in a period during which the gradient pulse is applied, and remove the noise mixed into the ECG signal in the period during which the gradient pulse is applied, by using noise estimated by the adaptive filter.

2. The ECG signal processing apparatus according to claim 1,
wherein the processing circuitry is configured to
implement the adaptive filter as an FIR (Finite Impulse Response) filter having variable coefficients, and
update the filter coefficients of the adaptive filter in such a manner that similarity between the first parameter stored in the memory circuitry and a second parameter extracted from an ECG signal subjected to noise removal processing is enhanced.

3. The ECG signal processing apparatus according to claim 2,
wherein the processing circuitry is configured to stop update of the filter coefficients of the adaptive filter in a period during which the gradient pulse is not applied.

4. The ECG signal processing apparatus according to claim 1,
wherein the processing circuitry is configured to
store an ECG spectrum expressed in a frequency domain and acquired in a period during which the gradient pulse is not applied, as the first parameter in the memory circuitry,
transform the ECG signal acquired from the electrocardiograph into the ECG spectrum,
transform the gradient magnetic field signal acquired from the MRI apparatus into a gradient magnetic field spectrum expressed in a frequency domain,
estimating the noise for each of predetermined frequency bands in a frequency domain, by using the gradient magnetic field spectrum and the ECG spectrum stored in the memory circuitry, and
remove the noise for each of the predetermined frequency bands in a frequency domain.

5. The ECG signal processing apparatus according to claim 4,
wherein the processing circuitry is configured to extract a power spectrum of a waveform including a peak value of an R-wave of the ECG signal in a period during which the gradient is not applied, as the first parameter.

6. The ECG signal processing apparatus according to claim 4,
wherein the processing circuitry is configured not to update filter coefficients corresponding to a frequency band in which cardiac action potential is included, out of plural filter coefficients of the adaptive filter.

7. The ECG signal processing apparatus according to claim 1,
wherein the processing circuitry is configured to
extract a waveform of the ECG signal acquired from the electrocardiograph in a period during which the gradient is not applied, as the first parameter,
estimate a waveform of the noise, by using a waveform of the gradient magnetic field signal and a waveform of the ECG signal acquired in a period during which the gradient pulse is not applied, and
remove the noise in a time domain according to the estimated waveform of the noise.

8. The ECG signal processing apparatus according to claim 1,
wherein the processing circuitry is configured to
acquire an operation signal indicating whether the gradient pulse is currently applied or not from the MRI apparatus, and
extract the first parameter from the ECG signal in a period during which the operation signal indicates that the gradient pulse is not applied.

9. The ECG signal processing apparatus according to claim 8,
wherein the processing circuitry is configured to sequentially update the first parameter stored in the memory circuitry by sequentially extracting the first parameter from the ECG signal, in a period during which the operation signal indicates that the gradient pulse is not applied.

10. The ECG signal processing apparatus according to claim 1,
wherein the processing circuitry is configured to estimate the noise from a sum signal obtained by summing up three gradient magnetic field signals in respective tri-axial directions orthogonal to each other.

11. An MRI apparatus configured to be connected with an electrocardiograph, the MRI apparatus comprising:
a gradient coil configured to apply a gradient pulse;
memory circuitry;
processing circuitry configured to
store a parameter of an ECG signal acquired from the electrocardiograph in a period during which the gradient pulse is not applied, as a first parameter in the memory circuitry,
implement an adaptive filter for estimating noise mixed into the ECG signal due to the gradient pulse, by using the first parameter stored in the memory circuitry and a gradient magnetic field signal in a period during which the gradient pulse is applied,
remove the noise mixed into the ECG signal in the period during which the gradient pulse is applied, by using noise estimated by the adaptive filter, and
generate a synchronization signal for ECG synchronization imaging by detecting an R-wave included in the ECG signal from which the noise is removed; and
an MRI control circuit configured to acquire magnetic resonance signals from an object in synchronization with the synchronization signal by controlling the gradient coil and generate an image of the object from the magnetic resonance signals.

12. An ECG signal processing method comprising:
storing a parameter of an ECG signal as a first parameter in memory circuitry, the ECG signal being acquired from an electrocardiograph operating in combination with an MRI apparatus in a period during which a gradient pulse is not applied by the MRI apparatus;
estimating noise mixed into the ECG signal due to the gradient pulse with an adaptive filter, by using the first parameter stored in the memory circuitry and a gradient magnetic field signal acquired from the MRI apparatus in a period during which the gradient pulse is applied; and
removing the noise mixed into the ECG signal in the period during which the gradient pulse is applied, by using estimated noise.

* * * * *